United States Patent
Ueda

(10) Patent No.: US 6,702,210 B1
(45) Date of Patent: Mar. 9, 2004

(54) GARBAGE DISPOSING DEVICE

(75) Inventor: Yasuichi Ueda, Okinawa (JP)

(73) Assignee: Japan Life Center, Inc., Okinawa (JP)

( * ) Notice: Subject to any disclaimer, the term of this patent is extended or adjusted under 35 U.S.C. 154(b) by 0 days.

(21) Appl. No.: 10/009,697

(22) PCT Filed: May 7, 1999

(86) PCT No.: PCT/JP99/02382

§ 371 (c)(1),
(2), (4) Date: Nov. 5, 2001

(87) PCT Pub. No.: WO00/67927

PCT Pub. Date: Nov. 16, 2000

(51) Int. Cl.[7] .............................................. B02C 25/00
(52) U.S. Cl. ...................................... 241/36; 241/282.2
(58) Field of Search ........................... 241/282.1, 282.2, 241/33, 36, 165.5

(56) References Cited

U.S. PATENT DOCUMENTS 3,845,939 A * 11/1974 Waldenville ............. 366/151.1
6,139,793 A * 10/2000 Vanderwal ..................... 422/1

FOREIGN PATENT DOCUMENTS

| JP | 9-234498 | 9/1997 |
| JP | 10-180228 | 7/1998 |
| JP | 51-145767 | 12/1999 |

* cited by examiner

*Primary Examiner*—Mark Rosenbaum
(74) *Attorney, Agent, or Firm*—Leighton K. Chong; Ostrager Chong & Flaherty (Hawaii)

(57) ABSTRACT

A garbage disposing device 1 comprises a disposing tank 10 of substantially the inverted-conical shape for storing organic substance such as garbage and fermentation accelerator additives in which fermentation microorganism is seeded beforehand in a sealed condition, a rotating shaft 12 which passes vertically through the disposing tank 10 and is driven to rotate by a motor connected to the lower or upper end thereof, a plurality of cutter blades 14 which are fixed in a cantilevered fashion to the rotating shaft 12 at intervals in the vertical direction for grinding and mixing the fermentation accelerator additive and the organic substance, and a plurality of thermo sensors 16 for detecting the temperatures of the disposing tank at a plurality of portions positioned at intervals in the vertical direction. Grinding and mixing can be performed sufficiently due to the fact that rotating resistance is small at all vertical positions of the disposing tank 10 because it is formed in the inverted-conical shape and grinding and mixing is performed by a plurality of cutter blades 14 mounted on the rotating shaft 12.

5 Claims, 5 Drawing Sheets

GARBAGE DISPOSING DEVICE

U.S. patent application claims the priority of PCT International Application No. PCT/JP99/02382, filed on May 07, 1999.

FIELD OF THE INVENTION

The present invention relates to a middle-sized garbage disposing device that ferments and disposes of organic substance such as leftovers and raw garbage and changes them into compost in a short time efficiently.

BACKGROUND OF THE TECHNOLOGY

Conventionally, a middle-sized garbage disposing device that disposes and changes raw garbage into compost is recognized as the middle size of a small device for a household and a big one for industry that is equipped with a grinding device, a mixing device and a fermentation disposal tank. A typical example of the middle size garbage disposing device is shown in FIG. 3. As indicated, a conventional garbage disposing device 3 comprises a generally cylindrical disposing tank 30 for storing organic substances such as garbage and a fermentation accelerator additive in which fermentation microorganism is seeded beforehand in a sealed condition, a rotating shaft 32 which passes vertically through the disposing tank 30 and is driven to rotate by a motor (not shown) connected to the lower end of the disposing tank, a cylinder 33 having a peripheral wall that is disposed at the upper side of and concentrically around the rotating shaft 32 and has many holes 33a thereon, and a screw blade 34 which is set in a spiral and is disposed on the rotating shaft 32 extending from below to the inside of the cylinder 33.

The method of using this garbage disposing device is as follows. As preparation process, a predetermined amount of the fermentation accelerator additive 35 in which the fermentation microorganism is seeded beforehand is put on bottom of the disposal tank. This additive 35 is made up of bacteria that is cultured from many kinds of microorganism in the soil and small wood chips of wood. Raw garbage (maximum 500 kg) is thrown to the additive from a raw garbage entrance 30a of the disposing tank 30. The motor is driven to rotate the rotating shaft 32 at a speed of 70 rounds/min. The fermentation accelerator additive 35 and the raw garbage are guided in the cylinder 33 by the screw blades 34 fixed on the rotating shaft 32 and are elevated on the inside thereof. Since there are many holes 33a on the cylinder 33, the fermentation accelerator additive and the raw garbage are subjected to cutting so that they are broken into small pieces, are pressed into the holes 33a and fall down on the bottom of the disposing tank 30.

In this way, after they are ground and mixed sufficiently, the motor is stopped and they are left, for example, to ferment for two or three days. During this time period, the raw garbage is resolved into carbonic acid gas and water due to work of bacteria so that good and homogeneous compost is produced.

Considering from the view point of processing efficiency in said raw garbage disposing device 3, it is necessary to grind and mix the fermentation accelerator additive and organic substance sufficiently as well as to process the fermentation disposal equally at the upper, the middle and the lower parts of the disposing tank 30. FIG. 4 represents the temperature change in the lower tank of the disposing tank 30 in case that the raw garbage was thrown into the disposing tank 30 of the conventional garbage disposing device 3 at levels of 40 cm, 55 cm 67 cm height, respectively. (The experiment for each height was done twice.) As a result, it was found that the fermentation disposing progresses rapidly in proportion to the amount of the raw garbage put into the disposing tank 30 as long as the motor rotating the rotating shaft 32 permits. In other words, when the fermentation disposal progressed, the temperature of disposal materials thrown into and ground and then mixed was increasing. As it is shown in FIG. 4, the higher the amount of raw garbage thrown into, the higher the temperature of the fermentation disposal was or the fermentation progressed.

Next, the raw garbage was thrown into the disposing tank at 30 to 65 cm in height, and the change of the temperature in the lower, middle and upper parts of the disposing tank were checked under the same condition as described above (refer to the FIG. 5). As a result, there was more than 10 degrees difference in temperature between the lower and the upper part of the disposing tank 30 during a period from 30 minutes to two hours after the beginning of disposing. Furthermore, there was a drawback that the progress of disposing became slow, in the case of only 5~6 degree difference in temperature even after 7 hours passed from the beginning of disposing.

The purpose of the present invention is to solve the above drawback of the conventional garbage disposing device and offer a garbage disposing device that is able to perform fermentation disposal at almost the same processing condition at all heights of a disposing tank.

DESCRIPTION OF THE INVENTION

The present invention to solve the above drawback provides a garbage disposing device which comprises a disposing tank having a decreasing radius in a horizontal cross section downwardly for storing an organic substance such as garbage and fermentation accelerator additives in which fermentation microorganism is seeded beforehand in a sealed condition, a rotating shaft which passes vertically through the disposing tank and is driven to rotate by a motor connected to the lower or upper end of the disposing tank, a plurality of cutter blades which are fixed in a cantilevered fashion to the rotating shaft at intervals in the vertical direction for grinding and mixing the fermentation accelerator additive and the organic substance, and a plurality of thermo sensors for detecting the temperature of the disposing tank at a plurality of portions positioned at intervals in the vertical direction.

Grinding and mixing can be performed sufficiently with small rotating resistance at various vertical positions of the disposing tank because the disposing tank is formed to have the decreasing radius in horizontal cross section downwardly and the grinding and mixing is performed by the plurality of cutter blades mounted on the rotating shaft.

The present invention is also characterized in that the disposing tank forms an inverted-conical shape with an inclination to the vertical direction of 20–50 degrees.

With this range of inclination angle, the rotating resistance loaded over the cutter blades becomes small and the device is efficient, because it is supported by the wall that supports a part of the load from the upper part of the raw garbage that is thrown or put into the disposing tank.

The present invention is also characterized in that the height of the disposing tank is 100 cm or less.

To perform grinding and mixing the fermentation accelerator additive and the organic substance sufficiently, the device needs a rotating speed of about 110 rounds/min. With a general-use motor available at low cost, the height of the disposing tank is formed to 100 cm or less to avoid excessive load to the motor.

The present invention is also characterized in that an entrance for the organic substance into the disposing tank is formed on the top and an outlet of disposed compost is formed at the bottom of this disposing tank.

By forming the entrance for the organic substance on the top of the disposing tank, the organic substance can be thrown into the disposing tank easily just by releasing the organic substance above the entrance. By forming the outlet for the disposal compost at the bottom of this disposing tank, all compost can be discharged outside of the disposing tank easily, because it falls down to be gathered toward the bottom of the disposing tank due to the decreasing radius in horizontal cross section downwardly and the inverted conical shape along the slope of the tank.

The present invention is also characterized in that it checks or monitors the temperature of disposing at least in the upper, middle and lower parts of the disposing tank and detects the transitions in the temperature increasing, the temperature staying constant and the temperature decreasing, and re-grinds and re-mixes the material by rotating the motor as needed, discharges the disposed compost from the bottom of the disposing tank, and/or throws or puts new organic substance such as raw garbage into this disposing tank.

The progress of the fermentation disposal can be detected from the temperatures at various positions of the disposing tank and is controlled using the temperatures as parameters to make fermentation disposal throughout the disposing tank homogeneous and efficient.

THE BEST MODE FOR CARRYING OUT THE INVENTION

A detailed explanation of the best mode of the garbage disposing device according to the present invention will be made referring to the above-noted drawings.

Figure 1:
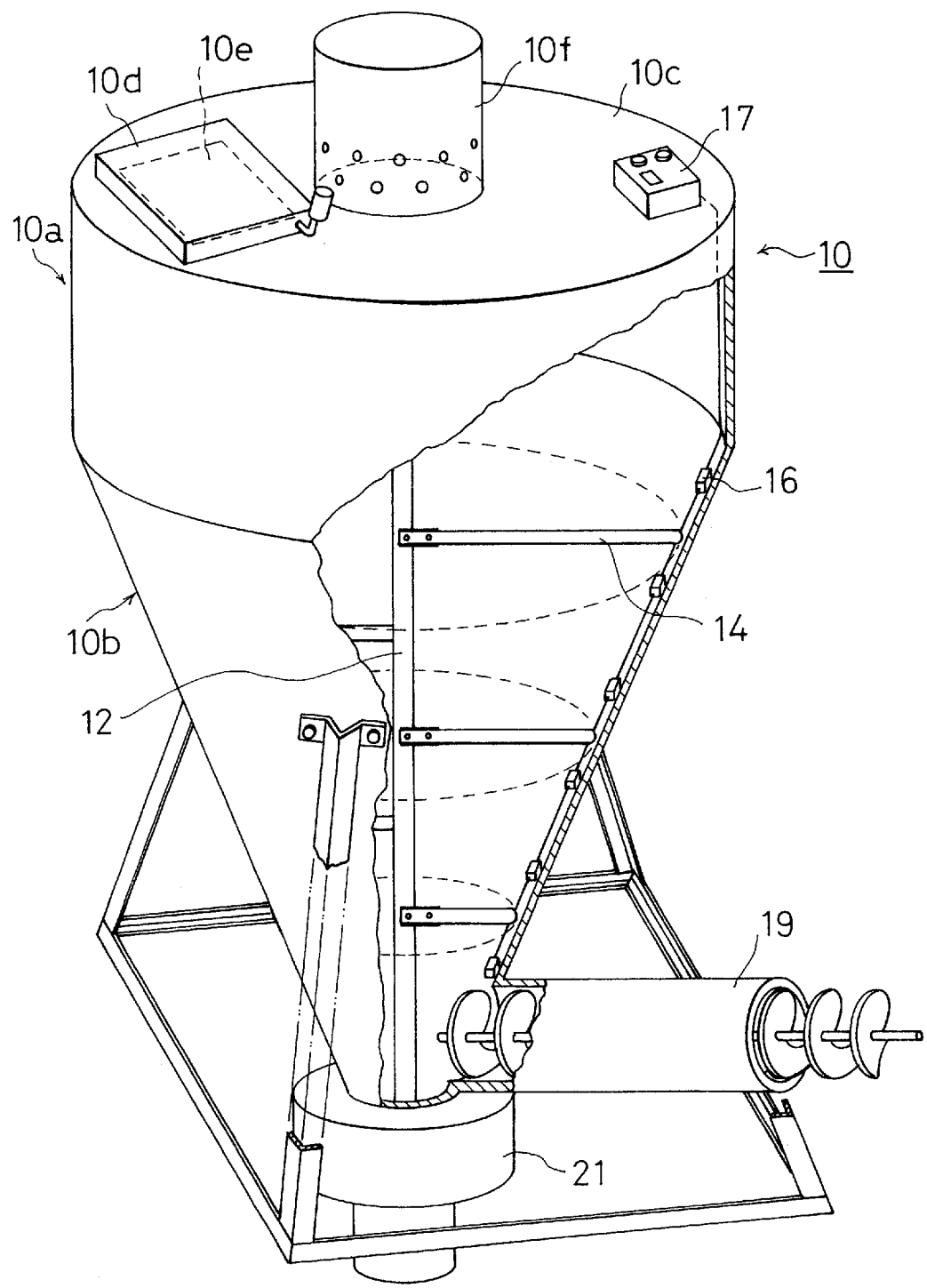
FIG. 1 is a general schematic view showing an embodiment of a garbage disposing device according to the present invention.

As shown in FIG. 1, a garbage disposing device 1 according to the present invention comprises a generally inverted-conical disposing tank 10, a rotating shaft 12 which passes vertically through and is supported by the disposing tank, a plurality of cutter blades 14 which are fixed to the rotating shaft at intervals in the vertical direction and a plurality of thermo sensors 16 for detecting temperatures in the disposing tank at a plurality of portions positioned at intervals in the vertical direction.

The disposing tank 10 is a container that can be stored in a sealed fashion. The disposing tank 10 is made of a metallic material having mechanical strength and durability and is formed to a substantially inverted-conical shape. In the preferred embodiment as shown, a cylinder part 10a is provided at the upper portion of the disposing tank 10. This cylinder part 10a has a space to store raw garbage the amount of which is more than that of disposing material ground and mixed in an inverted-conical part 10b. Raw garbage is reduced in volume by grinding and is further reduced in ume as fermentation disposing progresses, so that the raw garbage stored in the cylinder part 10a falls down into the inverted-conical part 10b. In that situation, it needs to drive the motor to grind and mix the disposing material again, because the raw garbage in the cylinder part 10a is not grounded and mixed yet.

A top 10c of the disposing tank 10 is provided with a raw garbage entrance 10e covered with a lid 10d that is capable of opening and closing and an exhaust duct 10f that discharges carbonic acid gas and steam produced in the disposing tank 10. Also, a control board 17 is set at the top 10c. The control board receives signals from a plurality of thermo sensors 16 and controls appropriately in accordance with commands set in advance.

The reserved-conical part 10b of the disposing tank 10 is formed in an inverted-conical shape at an inclination to the vertical direction of 20–50 degrees. With this range of angle, the rotating resistance loaded over the cutter blades 12 becomes small and the device is made efficient, because it is supported by the wall that holds a part of the load from the upper part of the raw garbage that is thrown or put into the disposing tank.

At a bottom of this disposing tank 10, a screw conveyor 19 that discharges disposed compost is provided. All compost can be discharged outside of the disposing tank easily, because it falls down toward the bottom along the slope of the inverted-conical part 10b of the disposing tank 10.

At the lower end of the rotating shaft 12, a general-purpose motor 21 of the type available at low cost is provided. To perform grinding and mixing of the fermentation and organic substance (disposing material) sufficiently, it needs to rotate the rotating shaft 12 at about 110 rounds/min. When the general-purpose motor is used, the height of the disposing tank 10 is kept to 100 cm or less to avoid excessive load to the motor.

Also, a plurality of cutter blades 14 are fixed to the rotating shaft 12 in a cantilevered fashion by using fastening members such as bolts and nuts at intervals in the vertical direction. In a preferred embodiment shown in the drawing, the cutter blades 14 are thin and made of metal, but of course any other forms of cutter blades may be used.

Experiment

The fermentation accelerator additive in which the fermentation microorganism is seeded beforehand and the raw garbage were thrown into the disposing tank 10 to 65 cm in height and the rotating shaft 12 was rotated at the speed of 110 rounds/min for 15 minutes. After the fermentation accelerator additive and raw garbage were ground and mixed sufficiently, we checked the temperatures in the lower, the middle and the upper parts of the disposing tank 10 by using the thermo sensors 16 (refer to FIG. 2).

Figure 2:
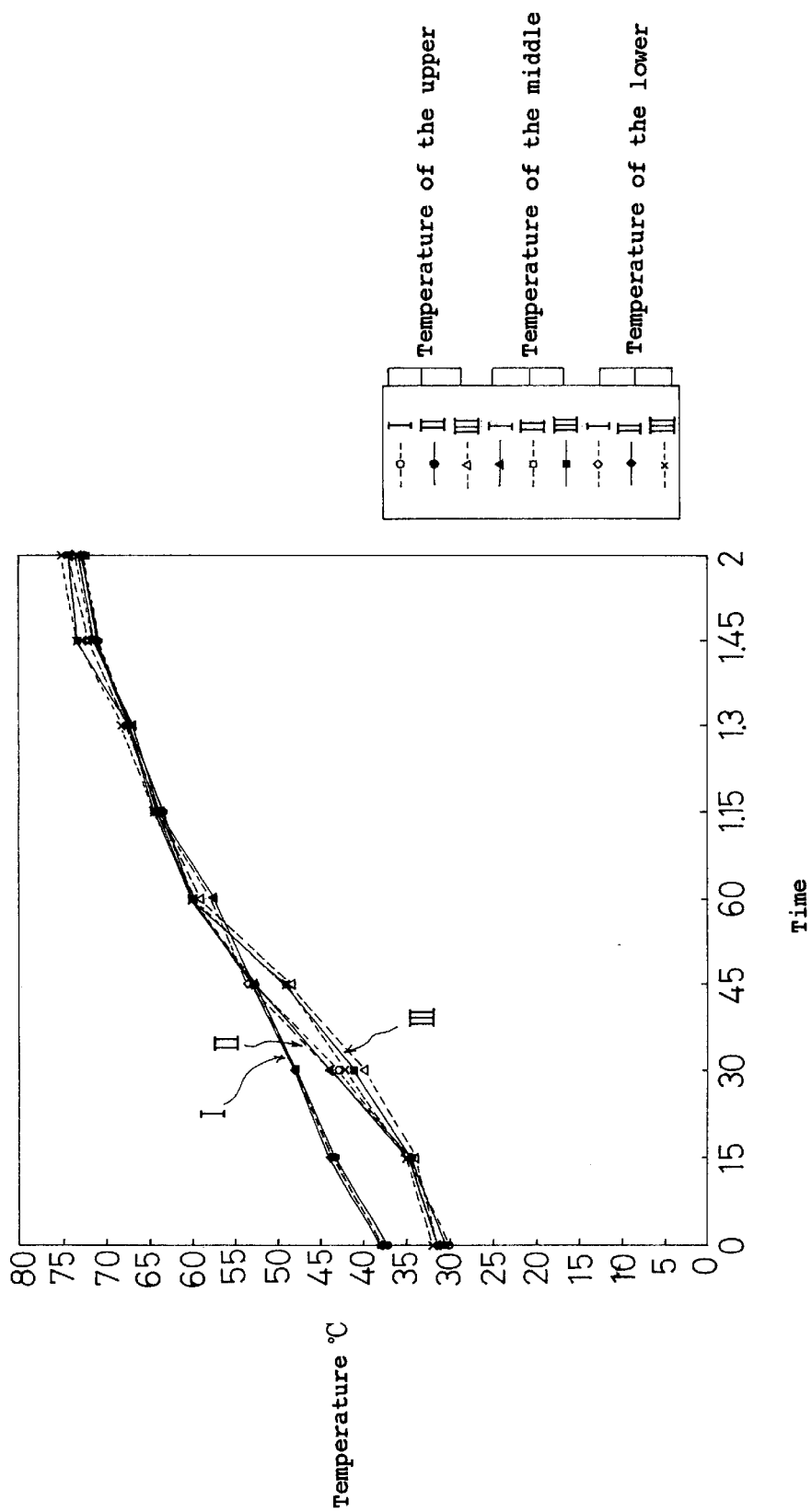
FIG. 2 is a graph showing the change of the temperature in the lower, middle and upper parts of the disposing tank wherein raw garbage is disposed in the garbage disposing device according to the present invention.
Figure 3:
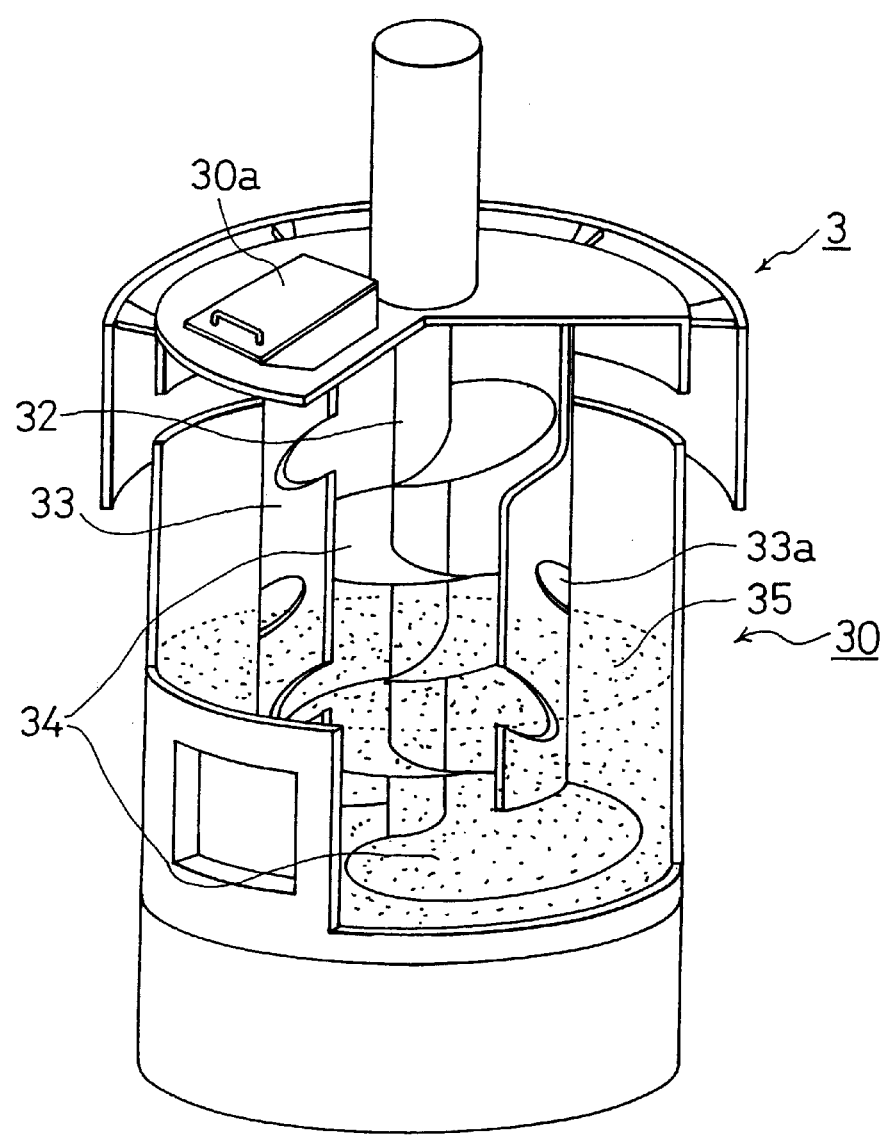
FIG. 3 is a general schematic view of the conventional garbage disposing device.
Figure 4:
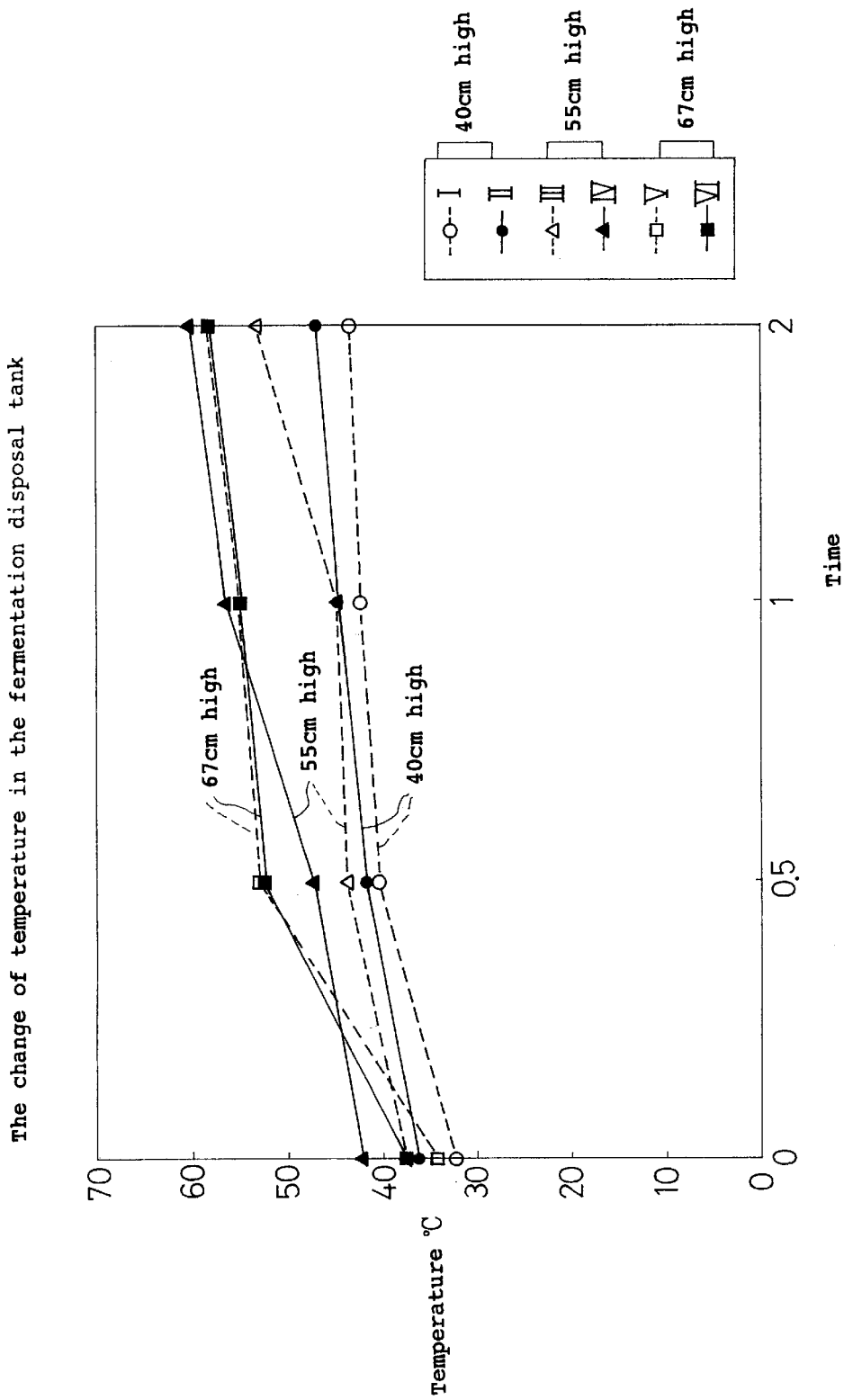
FIG. 4 is a graph showing the change of temperature at the lower part of the disposing tank wherein raw garbage is put into the disposing tank of FIG. 3 to 40 cm, 55 cm and 67 cm heights and then subjected to fermentation disposal.
Figure 5:
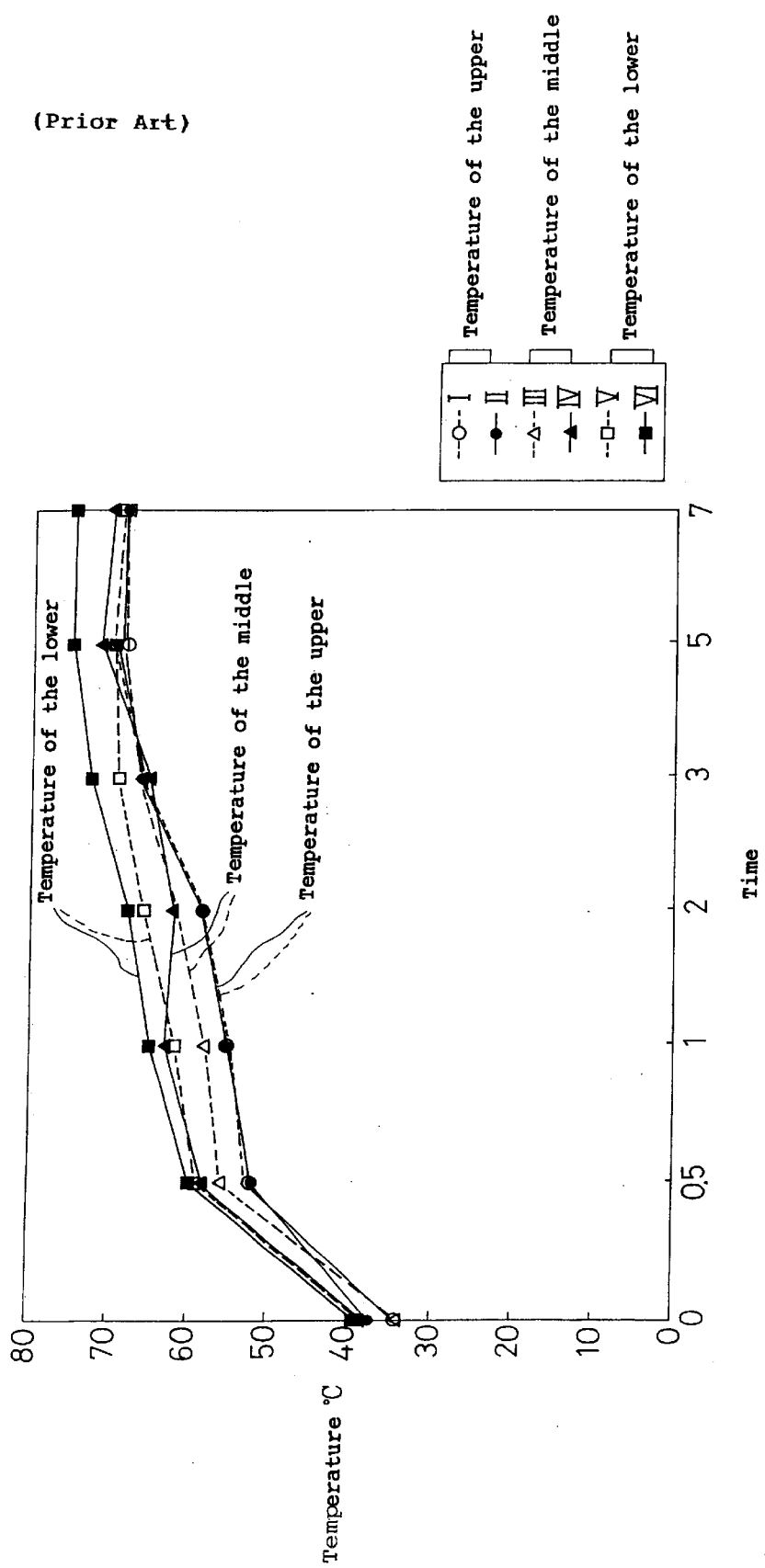
FIG. 5 is a graph showing the change of temperature in the lower, middle and upper parts of the disposal tank wherein raw garbage is subjected to fermentation disposal using the garbage disposing device of FIG. 3.

As it is indicated in FIG. 2, there was about 5 degrees difference in temperature between the lower, the middle and the upper parts of the disposing tank 10 for 45 minutes after starting to rotate the motor 21. However, when it passed 60 minutes after starting to rotate the motor 21, there was little difference in temperature between them. Furthermore, it entered into the temperature of about a 75 degree zone, when it passed 2 hours after starting to rotate the motor 21. It improved the speed of fermentation greatly, compared to 7 hours in the case of FIG. 5. And also, the temperature itself in the constant temperature period is up 2 to 5 degrees compared to the case of FIG. 5 and the processing efficiency is improved.

The grinding and mixing can be performed sufficiently by a plurality of cutter blades 14 mounted on the rotating shaft 12 due to the fact that the rotating resistance is small at all vertical positions of the disposing tank 10 because the disposing tank 10 is formed in the inverted-conical shape.

In the garbage disposing device 1 according to the present invention, the cost is kept low because it does not need a grinding device. Although the heads of fishes and bones of pigs are left in compost as bones, all parts of meat are subjected to fermentation disposal and changed to compost. The bones in the compost can be separated from the compost by using a sieve easily.

What is claimed is:

1. A garbage disposing device comprise comprising, a disposing tank having an inclined wall of substantially the inverted-conical shape for storing organic substance such as garbage and fermentation accelerator additives in which fermentation microorganism is seeded beforehand in a sealed condition, a rotating shaft which passes vertically through the disposing tank and is driven to rotate by a motor connected to the lower or upper end of the disposing tank, a plurality of cutter blades which are fixed in a cantilevered fashion to the rotating shaft at intervals in the vertical direction for grinding and mixing the fermentation accelerator additive and the organic substance in a vertical range of the inclined wall of the disposing tank is inclined, and which has a length to extend adjacent to the inclined wall of the disposing tank, and a plurality of thermo sensors for detecting temperatures in the disposing tank at a plurality of portions positioned at intervals in the vertical direction.

2. The garbage disposing device defined in claim 1 being characterized in that the inclined wall of the disposing tank forms an inverted-conical shape inclination to the vertical direction of 20–50 degrees.

3. The garbage disposing device defined in claim 1 being characterized in that the height of the disposing tank is 100 cm or less.

4. The garbage disposing device defined in claim 3, characterized in that an entrance to the disposing tank is formed on a top of the disposing tank and an outlet for, disposed compost is formed at a bottom of this disposing tank.

5. The garbage disposing device defined in claim 1, characterized in that it checks or monitors temperature of disposing at least in the upper, middle and lower parts of the disposing tank and detects the transitions to temperature increasing, temperature staying constant and temperature decreasing, and re-grinds and re-mixes them by rotating the motor as needed, discharges the disposed compost from the bottom of the disposing tank, and/or receives new organic substance such as raw garbage into this disposing tank.

* * * * *